United States Patent [19]
Barritault et al.

[11] Patent Number: 6,103,880
[45] Date of Patent: *Aug. 15, 2000

[54] HARP FAMILY GROWTH FACTORS

[75] Inventors: Denis Barritault, Paris; José Courty, Villecresnes, both of France; Khalid Laaroubi, Sidi Kacem, Morocco

[73] Assignee: Valbiofrance, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/464,841

[22] PCT Filed: Feb. 25, 1994

[86] PCT No.: PCT/FR94/00219

§ 371 Date: Nov. 1, 1995

§ 102(e) Date: Nov. 1, 1995

[87] PCT Pub. No.: WO94/19462

PCT Pub. Date: Sep. 1, 1994

[30] Foreign Application Priority Data

Feb. 26, 1993 [FR] France ................... 93 02270

[51] Int. Cl.$^7$ .................................................. C07K 14/475
[52] U.S. Cl. ........................................... 530/399; 530/350
[58] Field of Search ...................... 530/350, 323, 530/326, 327, 305, 381, 412, 829, 399; 536/23.1, 23.5; 435/320.1, 240.2, 252.33; 514/2, 12, 13, 14, 15; 424/21, 198.1; 930/10

[56] References Cited

FOREIGN PATENT DOCUMENTS 0474979  3/1992  European Pat. Off. .

OTHER PUBLICATIONS

Rudinger, In "Peptide Hormones" (Jun. 1976)ed. J. A. Parsons, University Park Press, Baltimore, pp 1–7.
Courty et al. (1991) J. Cell Biochem. Suppl. 0 (15, part F): 221, abstract No. CF110.
Kretschmer et al. (1991) Growth Factors 5: 99–114.
Li et al. (1990) Science 250: 1690–1694.
Wellstein et al. (1992) J. Biol. Chem. 267: 2582–2587.
Huber et al. (1990) Neurochemical Res. 15 (4): 435–439.

*Primary Examiner*—Christina Y. Chan
*Assistant Examiner*—Robert C. Hayes
*Attorney, Agent, or Firm*—Bierman, Muserlian and Lucas

[57] ABSTRACT

Novel peptides having a SEQ ID No. 2 and SEQ ID No. 4 which peptides possess mitogenic properties.

1 Claim, 6 Drawing Sheets

HARP FAMILY GROWTH FACTORS

This is a 371 of PCT/FR94/00219, filed Feb. 25, 1994.

The object of the present invention is HARP family growth factors.

It also relates to preparation methods for these factors using genetic engineering techniques.

It also concerns applications of such factors in therapeutics.

Growth factors named HBBM have been detected during the purification of other growth factors of the FGFS (Fibroblast Growth Factor) group.

The HBBM have in particular been the object of a European patent application 89 101 187 (Publication No EP-326.075) in which their isolation from a brain extract, by a purification process including an extraction at acid pH and chromatography steps, is described. This process led to the isolation of three peptides of 18 kD, 16 kD and 15 kD with the same terminal sequence $NH_2$-GLY-LYS-LYS-GLU-LYS-PRO-GLU-LYS-LYS-VAL-LYS-LYS-SER-ASP-CYS-GLY-GLU-TRP-GLN-TRP-SER-VAL-CYS-VAL-PRO (SEQ ID NO:2, residues 4–15).

Application EP-326.075 describes a mitogenic activity of the HBBM on endothelial cells at concentrations of the order of 20 to 50 ng/ml, for the induction of a stimulation effect of 50%. of the maximum stimulation of proliferation, and a minimum effect from 3 ng/ml. At this concentration, the mitogenic effect of the HBBM was comparable to that of the acid form of the FGF (aFGF). This application also states that the three HBBM forms had angiogenesis promotion activity and activities of maintenance of the integrity and tissue cicatrization particularly for skin, bone and nerve tissues, but does not report experimental results.

In a subsequent article (Growth Factors, 4: 97–107, 1991), the inventors returned to the results described in patent EP-326.075 and showed that their new HBBM preparations, also obtained from beef brain, were in fact devoid of mitogenic activity, particularly for endothelial and fibroblast cells, even at concentrations of 1 to 10 µg/ml. The only activity confirmed was a neurotrophic activity giving neurite growth on rat embryo neurons at concentrations of between 80 and 640 ng/ml. The authors of this article thus decided to change the name of this factor to designate it by the new acronym HBNF for "Heparin Binding Neurotrophic Factor". The reason for these differences between the first work described in the patent application and that described subsequently was not clearly understood but the hypothesis advanced was that of a contamination by the growth factor bFGF during the first preparations. Factor bFGF was in fact already well known for its angiogenic and mitogenic activities and had been isolated by a similar procedure from brain.

In order to confirm their results on the absence of mitogenic and angiogenic activities of HBNF, the same authors purified HBNF from the expression product of the gene for this protein in bacteria (Kretschmer et al., Growth Factors, 5: 99–114, 1991). The protein obtained contained 168 amino acids and was purified after maturation in the form of a protein of 136 amino acids, whose sequence was identical to that previously described, beginning thus from the N-terminal end by the amino acids $NH_2$-GLY-LYS-LYS-GLU-LYS-PRO-GLU-LYS-LYS-VAL (SEQ ID NO:2, residues 4–13). This protein is devoid of mitogenic and angiogenic activities. Only the neurotrophic activity, comparable to that of the HBNF protein purified from brain, was confirmed.

By a comparable approach, another team of researchers showed that the same protein obtained by expression of the same gene, named HB-GAM by these authors and inserted into a baculovirus vector in insect cells, is also devoid of mitogenic activity (Raulo et al., J. Biol. Chem., 267, 1–9, 1992). The protein thus purified had an N-terminal sequence GLY-LYS-LYS-GLU-LYS (SEQ ID NO:1, residues 4–8) identical to that which these authors had obtained by an extraction from rat brain. This recombinant protein had a neurotrophic activity comparable to the native protein. The authors concluded that only the neurotrophic activity of HB-GAM existed. It was optimal at 200 ng/ml in the test used on the neuron cells cultivated on a medium recovered from the HB-GAM protein.

Analogous results, showing the absence of the mitogenic activity of this protein extract from beef brains, were also reported by other researchers working independently, see Molecular Biology of the Cell, 3: 85–93, 1992 and J. Biol. Chem., 265: 18749–18752, 1990. The neurotrophic activity was also described. The peptide sequence was identical to that of HB-GAM or HBNF with the N-terminal amino acid sequence GLY-LYS-LYS-GLU-LYS.

In parallel, the same protein (N-terminal sequence GLY-LYS-LYS-GLU-LYS) had been extracted from bovine uterus; this, named HBGF-8 and then Pleiotrophin (PTN) by the authors, had mitogenic activity on fibroblasts (Biochem. Biophys. Res. Commun., 165: 1096–1103, 1989). A year later, the same authors (Li et al., Science, 250: 1690, 1990) published the results of a transfection experiment of COS-7 eukaryotic cells and a transitory expression of the PTN gene. These authors showed that the cell lysate of the COS-7 cells transfected by the PTN gene was capable of inducing cell multiplication. However the molecular characterization of the PTN protein was not performed.

Yet other scientists have shown that mammary tumor cells secreted a growth factor capable of being retained by chromatography on heparin-Sepharose. This factor has been purified and its N-terminal peptide sequence is identical to that of HARP with the exception of the first amino acid which was not determined (WELLSTEIN et al., J. Biol. Chem., 267: 2582, 1992).

It is thus apparent from the state of the art described above that there is great uncertainty as to the structure of the molecule or molecules responsible for the mitogenic, angiogenic and neurotrophic activities described by the different authors.

A person skilled in the art could nevertheless assume, in view of these results, that the molecule or molecules isolated by the different groups had a common N-terminal having the following sequence:

$NH_2$-GLY-LYS-LYS-GLU-LYS-PRO-(SEQ ID NO:1, residues 4–9).

OBJECTS OF THE INVENTION

The applicant has thus aimed to discover molecules with well-determined structures, having the above activities at therapeutically useful levels.

The applicant has also aimed to develop a method of preparing these molecules in a form essentially free from contaminants.

THE INVENTION

The applicant has unexpectedly found that these molecules have sequences partially similar to those described previously, but extended by amino acids at their N terminal end, and biological activities greater than those described in the prior art.

The applicant has in addition shown that these molecules can be prepared in sufficient quantities, and in an almost pure form, by insertion and expression of a complementary DNA of this molecule into eukaryotic cells or into bacteria.

The object of the present invention is thus peptides having a similar sequence to peptide HARP and a mass of 18 kD and which may have an N-terminal end of the following sequence:
SEQ ID NO:1
NH₂-ALA-GLU-ALA-GLY-LYS-LYS-GLU-LYS-PRO-GLU-LYS-LYS They may advantageously have the following sequence:
SEQ ID NO:2
NH₂-ALA-GLU-ALA-GLY-LYS-LYS-GLU-LYS-PRO-GLU-LYS-LYS-VAL-LYS-LYS-SER-ASP-CYS-GLY-GLU-TRP-GLN-TRP-SER-VAL-CYS-VAL-PRO-THR—SER-GLY-ASP-CYS-GLY-LEU-GLY-THR-ARG-GLU-GLY-THR-ARG-THR-GLY-ALA-GLU-CYS-LYS-GLN-THR-MET-LYS-THR-GLN-ARG-CYS-LYS-ILE-PRO—CYS-ASN-TRP-LYS-LYS-GLN-PHE-GLY-ALA-GLU-CYS-LYS-TYR-GLN-PHE-GLN-ALA-TRP-GLY-GLU-CYS-ASP-LEU-ASN-THR-ALA-LEU-LYS-THR-ARG—THR-GLY-SER-LEU-LYS-ARG-ALA-LEU-HIS-ASN-ALA-GLU-CYS-GLN-LYS-THR-VAL-THR-ILE-SER-LYS-PRO-CYS-GLY-LYS-LEU-THR-LYS-PRO-LYS—PRO-GLN-ALA-GLU-SER-LYS-LYS-LYS-LYS-LYS-GLU-GLY-LYS-LYS-GLN-GLU-LYS-MET-LEU-ASP Peptides which are objects of the present application may also have an N-terminal end of the following sequence
SEQ ID NO: 3
NH₂-ALA-VAL-ASP-THR-ALA-GLU-ALA-GLY-LYS-LYS-GLU-LYS-PRO-GLU-LYS-LYS The peptides having a terminal end of the formula SEQ ID NO: 3 advantageously have at least in part the following sequence:
SEQ ID NO: 4
NH₂-ALA-VAL-ASP-THR-ALA-GLU-ALA-GLY-LYS-LYS-GLU-LYS-PRO-GLU-LYS-LYS-VAL-LYS-LYS-SER-ASP-CYS-GLY-GLU-TRP-GLN-TRP-SER-VAL—CYS-VAL-PRO-THR-SER-GLY-ASP-CYS-GLY-LEU-GLY-THR-ARG-GLU-GLY-THR-ARG-THR-GLY-ALA-GLU-CYS-LYS-GLN-THR-MET-LYS-THR-GLN-ARG—CYS-LYS-ILE-PRO-CYS-ASN-TRP-LYS-LYS-GLN-PHE-GLY-ALA-GLU-CYS-LYS-TYR-GLN-PHE-GLN-ALA-TRP-GLY-GLU-CYS-ASP-LEU-ASN-THR-ALA—LEU-LYS-THR-ARG-THR-GLY-SER-LEU-LYS-ARG-ALA-LEU-HIS-ASN-ALA-GLU-CYS-GLN-LYS-THR-VAL-THR-ILE-SER-LYS-PRO-CYS-GLY-LYS-LEU—THR-LYS-PRO-LYS-PRO-GLN-ALA-GLU-SER-LYS-LYS-LYS-LYS-LYS-GLU-GLY-LYS-LYS-GLN-GLU-LYS-MET-LEU-ASP The present invention also relates to fragments of the peptides defined above comprising at the minimum at the N-terminal ends one of the sequences SEQ ID NO:1 or SEQ ID NO:3.

Biologically active peptides having such an N-terminal sequence are all the more unexpected since it would be difficult for a person skilled in the art, having knowledge of the state of the art analyzed above, to predict that an addition of amino acids to the N-terminal sequence of the known peptide would considerable improve its biological activity.

In fact, predictions as to the effect of the addition, elimination or modification of an amino acid in a given structure are impossible in the current state of knowledge of protein structures, even with the aid of the most advanced modeling techniques.

Another object of the present invention is the preparation of the peptide or of its fragments as defined above by a general genetic engineering method, according to which vectors carrying at least part of the complementary DNA of the extended form of peptide HARP are expressed and the peptide is then extracted.

The method of preparing the peptide as described previously comprises a step of secretion of said peptide or of its fragments in culture media or of extraction, advantageously from mammalian cells transfected by a vector carrying at least part of the complementary DNA of peptide HARP, and a step of purification of said peptide.

Advantageously, said vector carries the sequence, or a part thereof, of the DNA sequence SEQ ID NO:5.

The present invention also relates to the use of the peptide or of one of its fragments, as defined above, as a mitogenic or neurotrophic agent or as an agent for stimulating tyrosine hydroxylase activity.

Such a peptide can thus be used for cicatrization of the skin and bone regeneration as well as the maintenance of the homeostasis of these tissues, in particular to control imbalances such as osteoporosis, as well as as an angiogenic agent, in particular for encouraging the vascularization of brain structures or of the nervous system.

An additional object of the present invention is pharmaceutical compositions containing the peptides and fragments described above in combination with one or more compatible and pharmaceutically acceptable diluents or carriers. Such compositions are advantageously formulated with a view to enteral or parenteral administration by the usual galenic methods.

The invention will be illustrated, without in any way being limited, by the following description, with reference to the attached diagrams in which:

EXAMPLES

Example 1

PRODUCTION OF THE PROTEIN ACCORDING TO THE INVENTION BY CLONING AND EXPRESSION IN MAMMALIAN CELLS

I. Materials and Methods

1. Materials

The radiolabeled products such as tritiated thymidine ($^3$H Tdr) were supplied by Dositek (France) and cytosine triphosphate labeled with phosphorus 32 by Amersham France.

The cell culture products were from Gibco (France), as were the Dulbecco modified Eagle medium (DMEM), geneticin (G418), penicillin, streptomycin and fungizone.

The newborn calf and bovine fetal serums were from Eurobio (France).

The cell lines used were PC12 (derived from Pheochomocytome) and the line from bovine brain capillary endothelial cells (BBC), plus NIH 3T3 cells.

The chromatography products (S-Sepharose, Mono-S, heparin-Sepharose) were from Pharmacia (Sweden).

The pAG60 plasmid was kindly supplied by Dr. A. Garapin of the Institut Pasteur, Paris and has been described by Colbere et al., J. Mol. Biol., 1981, 150, 1–14.

2. Methods a—Construction of the Eukaryotic Expression Vector Coding for the Protein According to the Invention.

Figure 1:
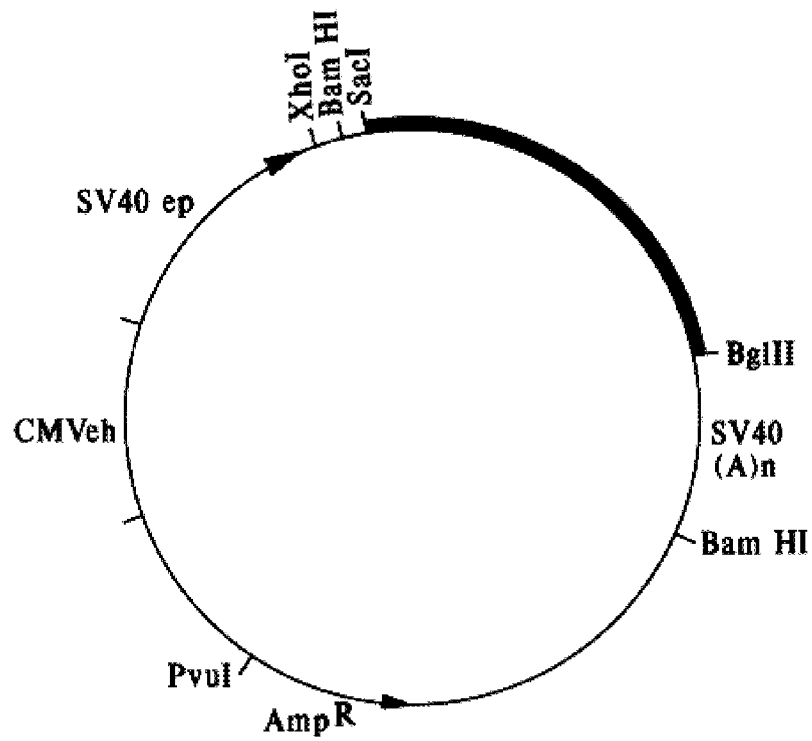
FIG. 1 is a schema of the plasmid named pJK12 used to transfect the mammalian cells.

The isolation of the complementary cDNA gene was carried out from a cDNA bank from human brain established in the lambda gtII system and from an oligonucleotide probe coding for a fragment of the HARP sequence (Asp-Cys-Gly-Glu-Trp-Gln). The gene thus isolated from this cone had the sequence SEQ ID NO:5. This gene was inserted into the expression vector containing the SV40 promoter and the human cytomegalovirus amplifier. The plasmid obtained, of 5.1 Kb, is shown in FIG. 1. The plasmid was named pJK12.

b—Transfections of Mammalian Cells.

The NIH 3T3 cells were cultured in DMEM medium in the presence of 10% newborn calf serum, penicillin (100 units per ml) and streptomycin (100 μg per ml). These cells were transfected in the presence of calcium phosphate as described by Chen and Okayama (Mol. Cell Biol., 1987, 7: 2745–2752).

The following transfections were carried out : 10 jg of pAG60 (plasmid resistant to neomycin) or the mixture containing 10 μg pJK12 and 1 μg pAG60 in the NIH 3T3 cells. After 48 hours, the cells were sub-cultured after 1/5th dilutions in a selection medium in the presence of antibiotic G418 at 400 μg/ml. This medium was renewed every 3 days and after 15 days colonies of cells resistant to G418 were detected growing in the culture medium.

Each clone selected was cultured independently and studied. After 2 sub-cultures, the cells were cultured in the normal culture medium (without antibiotic G418).

c—Selection of Cell Clone Secreting the Protein According to the Invention After Transfection.

In order to select a clone expressing the recombinant protein, the following experiments were carried out The culture medium obtained after 72 hours of culture of the cells of the studied transfected clone was collected. This culture medium was completed by Tris HCl buffer 10 mM, pH 7.5 and incubated for 2 hours at 4° C. with 150 ml of a solution of heparin-Sepharose (10% w/v in TE buffer 10 mM Tris HCl, pH 7.5, 1 mM EDTA). The heparin-Sepharose gel was then washed 4 times with a 0.6 M NaCl buffer and twice with the buffer alone.

The proteins retained on the heparin-Sepharose were eluted with 40 μl of the electrophoresis sample buffer described by Laemmli (Nature, 1970, 227: 680–685).

Analysis of the proteins by gel electrophoresis in the presence of sodium dodecyl sulfate was also carried out according to the same procedure of Laemmli. After electrophoresis, the gels were colored with silver according to the procedure described by wray et al. (Anal. Biochem., 1981, 118: 197–203).

d—Purification of the Recombinant Protein According to the Invention.

The purification of the human recombinant protein was carried out as described previously (Courty et al., Biochem. Biophys. Res. Commun., 1991, 151: 1312–1318).

In brief, starting with 1.2 liters collected of the conditioned medium, obtained after more than 72 hours of culture of the cells of the studied clone expressing the protein, the pH was adjusted to 6.00 with 100 mM of sodium phosphate (buffer A). This was centrifuged at 10 000 g for 15 minutes to remove cell debris and the cells which floated in the medium, and the supernatant was applied to a "fast flow" S Sepharose column.

This resin was washed with buffer A containing 0.15 M NaCl and the proteins were eluted with 0.6 M NaCl in the same buffer. This eluate was then applied onto a column of 1 ml of heparin-Sepharose using a pump with a flow rate of 0.5 ml per minute. The heparin-Sepharose column was previously equilibrated in Tris-HCl 10 mM, pH 7.5 and 0.5 M NaCl. The material not absorbed on the heparin-Sepharose column was removed; the column was washed exhaustively with the equilibration buffer until an absorption baseline of 280 nm was reached.

The elution of the proteins absorbed on the heparin-Sepharose column was then performed by increasing the NaCl concentration in the washing buffer. This increase was done in successive steps up to a concentration of 2 M NaCl.

Each fraction thus obtained was analyzed for its mitogenic activity according to the procedure described below. Neighboring fraction sharing mitogenic activity were combined and dialyzed against the 100 mM sodium phosphate buffer, pH 6.00 and containing 0.15 M NaCl. This fraction was then applied to a Mono S chromatography column at ambient temperature. The separation of the fractions was achieved with a linear NaCl gradient between 0.15 and 1 M in the same buffer. Each 1 ml fraction was examined for its mitogenic activity on the BBC cells.

e—Measurement of Mitogenic and Neurotrophic Activities.

The measurement of the mitogenic activities present in the different chromatographic fractions was carried out by measuring the increase of tritiated thymidine incorporation in BBC cells in culture according to the procedure described by Courty et al. (Biochem. Biophys. Res. Commun., 1991, 151: 1312–1318).

The measurement of the neurotrophic activity on the PC12 cells was carried out after sowing these cells at ten thousand cells per 35 mm diameter culture dish. These cells were placed in the presence of 3 ml of culture medium of which half was the conditioned medium obtained after 72 hours of culture of the cells of the clone resistant to the selection medium containing antibiotic G418. After 3 days, the neurite growth was estimated by comparison with that of control cells.

f—Microsequencing of the Proteins.

The microsequencing of the recombinant protein according to the invention was carried out according to conventional techniques described in numerous works. About 75 mmoles (1.3 µg) of the active fraction identified by Mono S was desalted by HPLC chromatography and injected into a gas-phase microsequencer (Applied Biosystems 470 A). The phenylthiohydantoin derivatives of the amino acids were identified by HPLC chromatography (model 120 A, Applied Biosystems).

II. Results.

1. Sequence of the cDNA of the Protein According to the Invention.

The sequence of the cDNA of the protein according to the invention SEQ ID NO:5 had characteristics common with those published by Kretschmer et al. (Growth Factors, 1991, 5: 99–144), except in the nontranslated 5' region, the sequence complementary to that described between bases 130 and 136, i.e. GGGAGGG, and three additional bases not described in positions 137, 138 and 139, i.e. GAG.

2. Detection of the Recombinant Protein According to the Invention.

Figure 2:
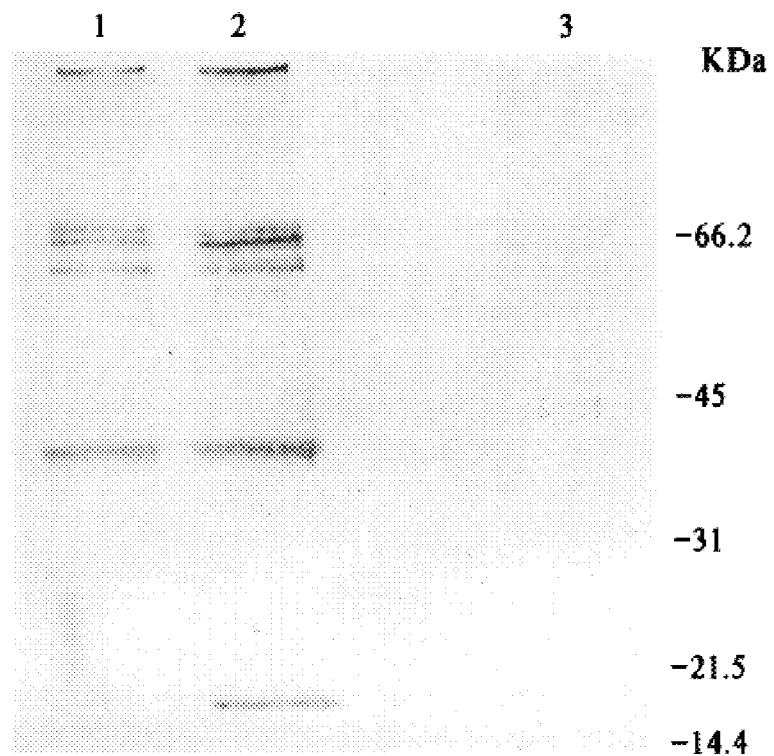
FIG. 2 represents an SDS-PAGE gel of supernatants of, respectively, a control cell clone (column 1), a clone transfected by the pJK12 plasmid (column 2) and protein HARP extracted from bovine brain.

The medium, conditioned for 72 hours, of two clones resistant to G418 was analyzed by SDS electrophoresis. FIG. 2 shows the existence of a polypeptide of 18 kD present specifically in the culture medium of the cells transfected by pJK12 (column no 2) while the medium conditioned by the control cells (transfected by the vector from which pJK12 originated but not carrying the cDNA, column no 1) did not contain this protein.

Column no 3 corresponds to the migration of protein HARP isolated from bovine brain.

3. Detection of the Neurotrophic Activity According to the Invention.

Figures 3A, 3B:
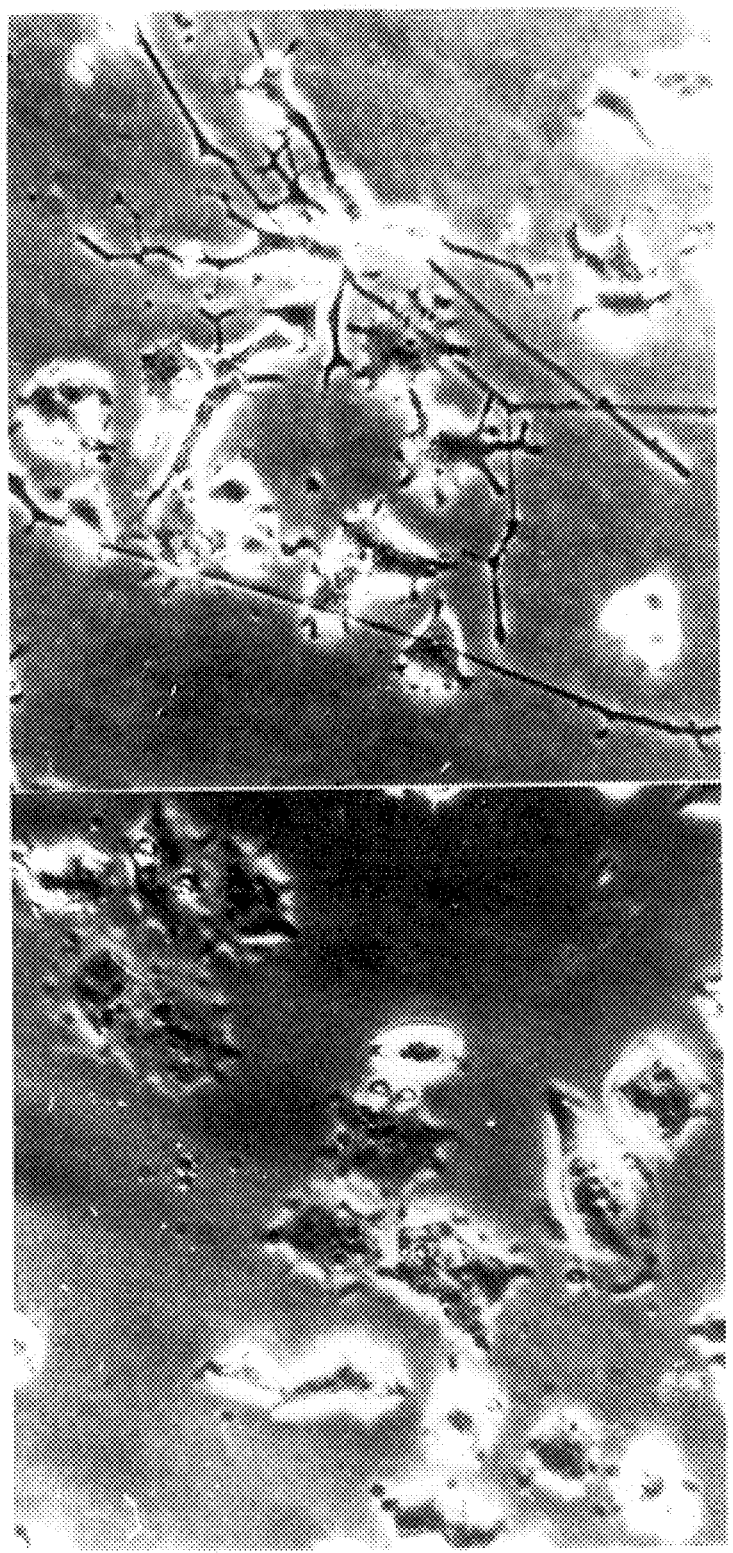
FIGS. 3A–B illustrates the effects on neurite growth of the PC12 line, by, respectively, a medium conditioned by control cells (3a) and a medium conditioned by cells transfected by the pJK12 plasmid (3b).

The neurotrophic activity of the PC12 cells was only detected in the medium conditioned by the cells transfected by the protein according to the invention, as shown in FIG. 3. A substantial increase in neurites can be noted in FIG. 3b compared to FIG. 3a.

4. Purification of the Protein According to the Invention and Characterization of its Mitogenic Activity.

The purification of the protein from the medium conditioned by the cells transfected by the pJK12 plasmid was carried out according to the procedure described above.

Figure 4:
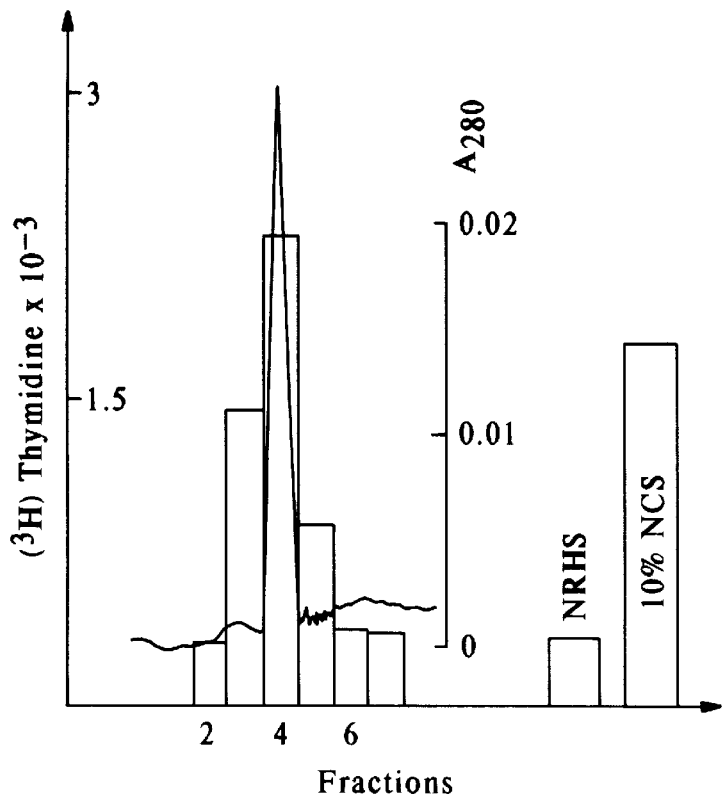
FIG. 4 represents the mitogenic activity of fractions obtained by chromatography on heparin-Sepharose of the medium conditioned by the cells transfected by the pJK12 plasmid. The mitogenic activity was evaluated by tritiated thymidine incorporated (as ordinate) while the absorbance of the fractions was measured at 280 nm (A 280). NRHS corresponds to the fraction not retained on the chromatography gel.

The biological activity profile of the protein obtained after elution from affinity chromatography on heparin-Sepharose is shown in FIG. 4. The fraction eluted at 2 M NaCl stimulated tritiated thymidine incorporation in the BBC cells.

Figure 5:
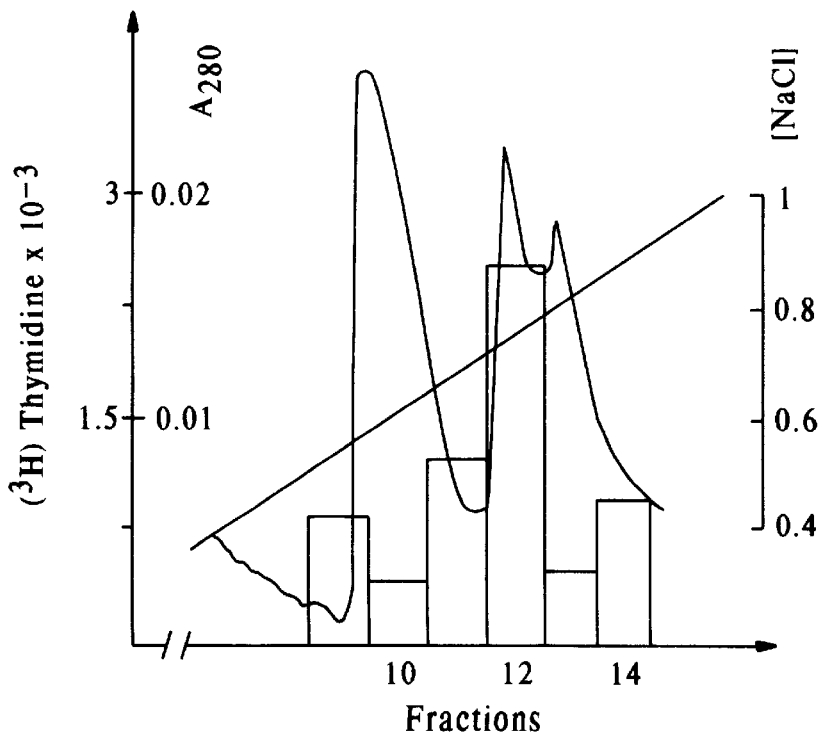
FIG. 5 illustrates the variation of the mitogenic activity of the fractions obtained by chromatography on Mono S, of the biologically active fraction previously obtained by heparin-Sepharose chromatography. NaCl represents the variation of the NaCl concentration in the elution gradient.

This mitogenic activity could be further fractionated by mono S chromatography as shown in FIG. 5.

Figure 6:
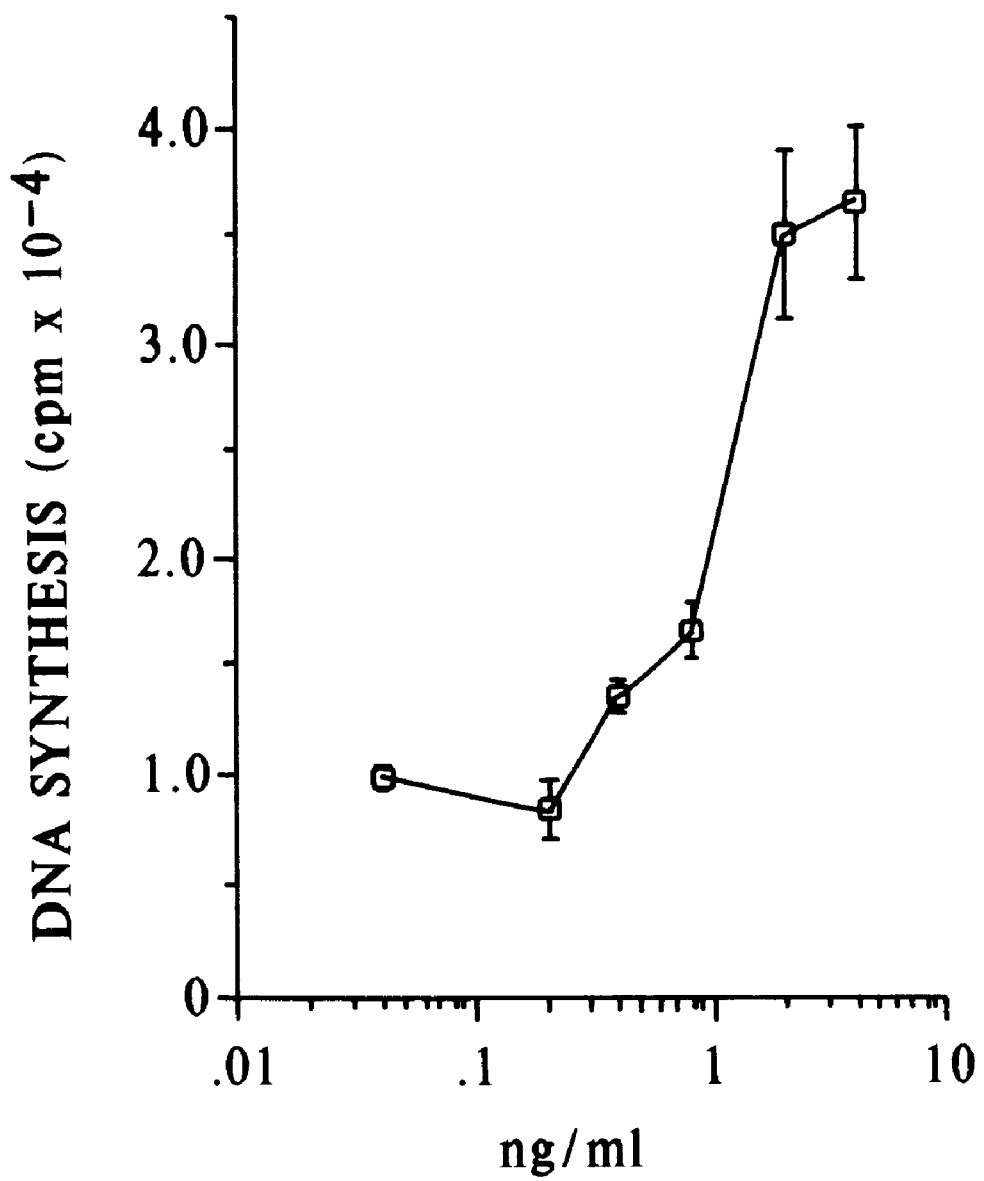
FIG. 6 represents the proliferation measured by the DNA synthesis (as ordinate) as a function of the recombinant protein concentration in ng/ml (as abscissa).

At a concentration of 0.8 M NaCl, a mitogenic activity was obtained and an examination of this activity as a function of concentration is illustrated in FIG. 6. The concentration of protein necessary to be added to the BBC cells in culture in the operating conditions described in the publication by Courty et al. (Biochem. Biophys. Res. Commun., 1991, 151: 1312–1318) was 55 pM (1 ng/ml) to obtain an effect half of the maximum incorporation of tritiated thymidine and 220 pM (4 ng/ml) to obtain the maximum (FIG. 6).

5. Study of the N-terminal Structure of the Recombinant Protein According to the Invention.

The biologically active fraction eluted at 0.8 M NaCl from the Mono S chromatography, present only in the medium conditioned by the cells transfected by the pJK12 plasmid, was injected after desalting by C4 HPLC chromatography into a microsequencer.

The sequence obtained was the following:

NH$_2$-ALA-GLU-ALA-GLY-LYS-LYS-GLU-LYS-PRO-GLU-LYS-LYS (SEQ ID NO:1)

No sequence GLY-LYS-LYS-GLU-LYS-PRO-GLU-LYS-LYS (SEQ ID NO:1, residues 4–12) was detected.

Example 2

PRODUCTION OF THE LONG (AEA) AND SHORT (GKK) FORMS OF PROTEIN HARP BY CLONING AND EXPRESSION IN *E. COLI*

With the aim of confirming the relationships existing between the presence of the three amino acids AEA at the N-terminal end and the biological activity of protein HARP, the two molecular forms of HARP were produced in *E. coli*.

1) Materials and Methods.

I. Construction of the Expression Vectors

In order to obtain the plasmids necessary to express protein HARP, two in vitro gene amplifications (PCR) were carried out from human cDNA coding for protein HARP. These amplifications were on the one hand carried out with the two following primers:

SEQ ID NO:6

5'-GCT GAA GCA GGG AAG AAA GAG-3'

SEQ ID NO:7

5'-GGT CTC GAG TAT GTT CCA CAG GTG ACA TC-3' thus generating a DNA coding for the form having three additional amino acids at the N-terminal end (AEA) and on the other hand with the two primers:

SEQ ID NO:8

5'-GGG AAG AAA GAG AAA CCA GAA-3'

SEQ ID NO:7

5'-GGT CTC GAG TAT GTT CCA CAG GTG ACA TC-3' generating a DNA coding for the short form (GKK).

The products from each amplification were analyzed on agarose gel, cleaved with suitable restriction enzymes and then purified by the agarase technique. The prokaryotic expression vector selected was pMAL-c (Biolabs) which contained a fusion protein MBP (maltose binding protein) coded by the gene MAL E. The construction was carried out according the recommendations described by Biolabs.

The cloning of the two amplification products in this vector was performed at the level of the polylinker thus linking during the expression the C-terminal portion of the MBP fusion protein to the N-terminal portion of protein HARP corresponding to the digestion site of factor Xa, which allowed protein HARP to be obtained after expression.

The two vectors thus obtained were introduced into *Escherichia coli* strain TB1, according to conventional techniques (Maniatis et al., 1982, Laboratory Manual, Cold Spring Harbor Laboratory).

2. Screening of the Clones Obtained:

The screening was carried out at the level of the bacterial plasmid DNA by searching for the cDNA coding for HARP, then by the capacity of the corresponding clone to produce the recombinant protein. These two screening techniques enabled us to select two clones: one coding for the long form of HARP (AEA) and the other for the short form of HARP (GKK).

3. Production of the Recombinant Protein:

20 ml of a pre-culture of each bacterial clone producing the long or short forms of protein HARP, were incubated in a liter of 2 YT medium at 37° C., then incubated in the presence of 0.3 mM of IPTG for 3 hours.

After this induction, the bacteria were centrifuged at 4000 g for 20 minutes and the resulting bacterial residue was resuspended in 50 ml of lysis buffer: 10 mM phosphate, pH 7, 30 mM NaCl, 0.25% Tween 20, 10 mM EDTA and 10 mM EGTA. The lysate was then frozen at −20° C. overnight.

After thawing, this lysate was sonicated, then cleared by centrifugation after the NaCl had been adjusted to a final concentration of 0.5M. The residue obtained was resuspended in 50 ml of a buffer made up of 50 mM Tris-HCl, pH 7.5, 6M guanidine HCl, the centrifuged for 15 minutes at 15000 g. The supernatant was then dialyzed for 24 hours at 4° C. against a buffer of 20 mM Tris HCl, pH 7.5, 2 mM $MgCl_2$ and 1 mM $CaCl_2$.

After dialysis, the precipitate formed was removed by centrifugation at 3000 g for 5 minutes and the supernatant, adjusted to a final concentration of 0.5M NaCl, was incubated with shaking with 0.5 ml of heparin-Sepharose overnight at 4° C. The gel was then washed with a buffer of 20 mM hepes, 0.5 M NaCl, then equilibrated with the buffer Tris-HCl 20 mM, pH 8, 100 mM NaCl and 2 mM $CaCl_2$. It was then incubated for 24 hours at 4° C. in the presence of factor Xa.

After digestion, the proteins HARP eluted from the gel with a buffer 20 mM hepes, pH 7.4 containing 2 M NaCl.

4. Test of Mitogenic Activity.

The mitogenic activity of the fractions obtained was determined by measuring the incorporation of tritiated thymidine into the nuclei of beef crystallin epithelial cells (BEL).

$1 \times 10^4$ BEL cells and 250 µl of DMEM medium containing 10% fetal calf serum were sown per well into a 48-well COSTAR culture plate.

After 48 hours of subculture, the medium was changed to DMEM medium without serum.

After 48 hours of incubation, the protein fractions to be tested were added, then after 16 hours culture under these conditions, 1 µCi of tritiated thymidine was added and the cells were reincubated for 6 hours. The TCA-precipitable radioactivity was then measured using a scintillation counter.

II. Results.

1. Production of the Fusion Protein.

In order to verify that the bacteria had correctly integrated the cDNAs coding for the long and short forms of protein HARP, an electrophoretic analysis of the recombinant proteins produced was performed.

0.5 ml of a bacterial culture coding for each of the forms of HARP, induced or not induced by 0.3 pM IPTG, was carried out according to the procedure described in Materials and Methods.

Each sample was centrifuged (4000 g, 20 min) and the resulting residue was resuspended in a SDS-PAGE buffer, then analyzed by electrophoresis containing 10% acrylamide.

Figure 7:
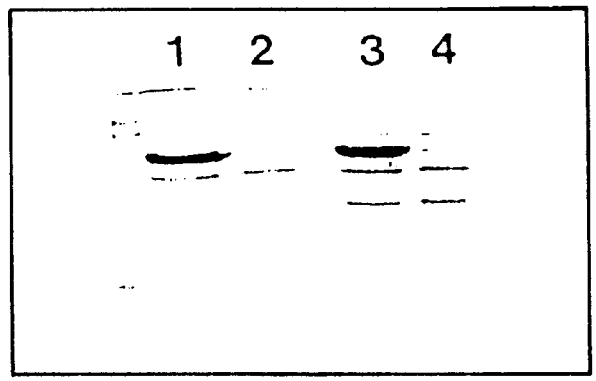
FIG. 7 is an electrophoretic analysis of the products synthesized by bacteria transformed by the plasmid coding for the long AEA and short GKK form of HARP. The bacterial lysates producing the AEA (track 1) or GKK forms (track 3) induced or not induced by IPTG (tracks 2, 4) were analyzed.

FIG. 7 shows the result of the electrophoresis colored with coomassie blue.

Analysis of this gel showed the presence of a major band corresponding to a molecular weight of 60 kDa (tracks 1 and 3) in the samples induced by IPTG.

This 60 kDa protein corresponded to the molecular weight of the fusion protein composed of the maltose binding protein (42 kDa) and HARP (18 kDa). No major band was detected in the samples not induced by IPTG (tracks 2 and 4).

This result shows that the bacteria had correctly integrated the plasmids coding for the long and short forms of the HARP molecule.

2. Electrophoretic Analysis of the Long (AEA) and Short (GKK) Forms of HARP.

100 ng of each of the proteins obtained after digestion by factor Xa, according to the technique described in materials and methods, were analyzed on 15% polyacrylamide gel. After migration, the gel was revealed by a silver coloration technique.

Figure 8:
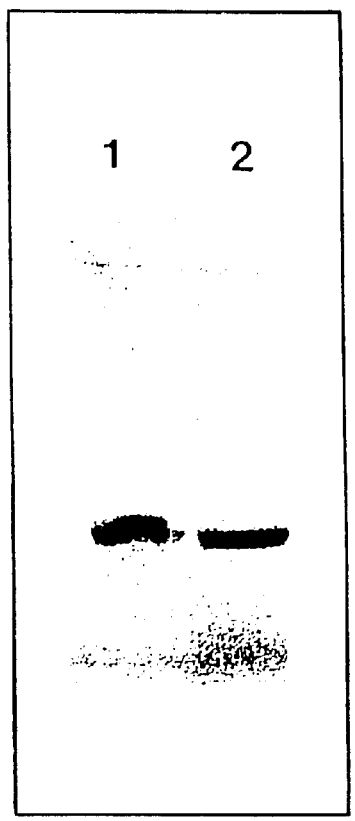
FIG. 8 is an electrophoretic analysis of the AEA (track 1) and GKK fractions (track 2) obtained after purification. After migration, the gel was colored with silver.

FIG. 8 shows the presence of a protein band corresponding to a molecular weight of 18 kDa for each of the forms AEA (track 1) and GKK (track 2).

3. Measurement of the Incorporation of Tritiated Thymidine Induced by the AEA and GKK Forms of HARP.

Figure 9:
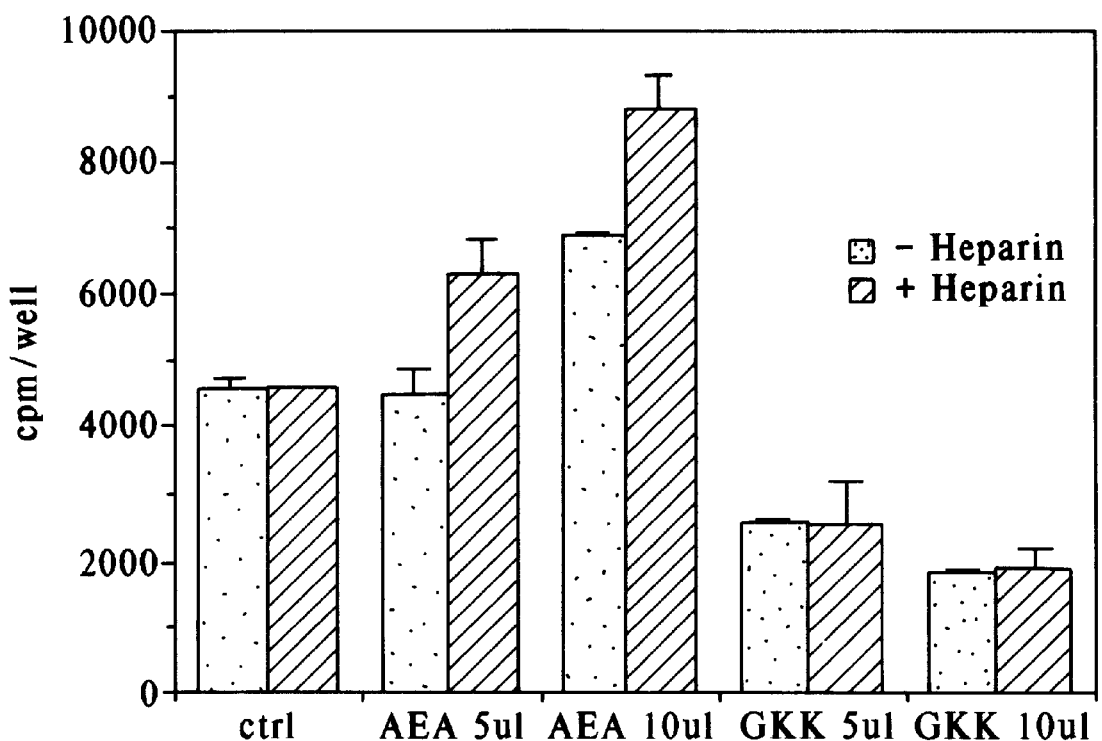
FIG. 9 shows the incorporation of tritiated thymidine induced by 10 μl (10 ng) or 5 μl (5 ng) of each of the molecular forms of protein HARP (AEA and GKK) incubated in the presence or absence of 125 ng of heparin in epithelial cells of beef crystallin.

The result of the incorporation of thymidine induced by each of the forms of HARP is shown on FIG. 9. The long form containing the sequence AEA at the N-terminal induced thymidine incorporation into BEL in a concentration-dependent manner. According to the concentrations used, this incorporation seemed to depend on the presence of heparin (500 ng/ml) in the culture medium. No mitogenic activity was detected for the short form of the HARP molecule (GKK) used at an equivalent concentration (10 ng/ml) to that of the long form (AEA).

Conclusion

The biological activity of the recombinant protein according to the invention obtained by secretion of mammalian cells transfected by a vector carrying a human cDNA or by production in E. coli is attributed to a polypeptide whose peptide sequence has the novel characteristic of having three additional amino acids at the N-terminal end, which are ALA-GLU-ALA.

The presence of these three additional amino acids enables the preparation of a biologically active form compared to protein HARP as previously described.

The activities are obtained at very low concentrations (around 1 ng/ml, i.e. 55 pM) of protein, by comparison with the concentrations reported in the prior art.

What is claimed is:

1. An isolated peptide consisting of:

SEQ ID NO:2
NH₂-ALA-GLU-ALA-GLY-LYS-LYS-GLU-LYS-PRO-GLU-LYS-LYS-VAL-LYS-LYS-SER-ASP-CYS-GLY-GLU-TRP-GLN-TRP-SER-VAL-CYS-VAL-PRO-THR—SER-GLY-ASP-CYS-GLY-LEU-GLY-THR-ARG-GLU-GLY-THR-ARG-THR-GLY-ALA-GLU-CYS-LYS-GLN-THR-MET-LYS-THR-GLN-ARG-CYS-LYS-ILE-PRO-CYS-ASN-TRP—LYS-LYS-GLN-PHE-GLY-ALA-GLU-CYS-LYS-TYR-GLN-PHE-GLN-ALA-TRP-GLY-GLU-CYS-ASP-LEU-ASN-THR-ALA-LEU-LYS-THR-ARG-THR-GLY-SER-LEU-LYS-ARG—ALA-LEU-HIS-ASN-ALA-GLU-CYS-GLN-LYS-THR-VAL-THR-ILE-SER-LYS-PRO-CYS-GLY-LYS-LEU-THR-LYS-PRO-LYS-PRO-GLN-ALA-GLU-SER-LYS-LYS-LYS-LYS—LYS-GLU-GLY-LYS-LYS-GLN-GLU-LYS-MET-LEU-ASP.

* * * * *

SEQUENCE LISTING (1) GENERAL INFORMATION:

(iii) NUMBER OF SEQUENCES: 8

(2) INFORMATION FOR SEQ ID NO: 1:

```
       (i) SEQUENCE CHARACTERISTICS:
            (A) LENGTH:  12
            (B) TYPE:  Amino Acid
            (C) STRANDEDNESS:  Unknown
            (D) TOPOLOGY:  linear (ii) MOLECULE TYPE: peptide (xi) SEQUENCE DESCRIPTION: SEQ ID NO: 1:

Ala Glu Ala Gly Lys Lys Glu Lys Pro Glu Lys Lys
 1               5                  10

(2) INFORMATION FOR SEQ ID NO: 2:

(i) SEQUENCE CHARACTERISTICS:
            (A) LENGTH:  139
            (B) TYPE:  Amino Acid
            (C) STRANDEDNESS:  Unknown
            (D) TOPOLOGY:  linear (ii) MOLECULE TYPE: peptide (xi) SEQUENCE DESCRIPTION: SEQ ID NO: 2:

Ala Glu Ala Gly Lys Lys Glu Lys Pro Glu Lys Lys Val
 1               5                  10

Lys Lys Ser Asp Cys Gly Glu Trp Gln Trp Ser Val Cys
         15                  20                  25

Val Pro Thr Ser Gly Asp Cys Gly Leu Gly Thr Arg Glu
                 30                  35

Gly Thr Arg Thr Gly Ala Glu Cys Lys Gln Thr Met Lys
 40                      45                  50

Thr Gln Arg Cys Lys Ile Pro Cys Asn Trp Lys Lys Gln
         55                  60                  65

Phe Gly Ala Glu Cys Lys Tyr Gln Phe Gln Ala Trp Gly
                 70                  75

Glu Cys Asp Leu Asn Thr Ala Leu Lys Thr Arg Thr Gly
 80                      85                  90

Ser Leu Lys Arg Ala Leu His Asn Ala Glu Cys Gln Lys
             95                 100

Thr Val Thr Ile Ser Lys Pro Cys Gly Lys Leu Thr Lys
105                 110                 115

Pro Lys Pro Gln Ala Glu Ser Lys Lys Lys Lys Lys Glu
         120                 125                 130

Gly Lys Lys Gln Glu Lys Met Leu Asp
                 135

(2) INFORMATION FOR SEQ ID NO: 3:

(i) SEQUENCE CHARACTERISTICS:
            (A) LENGTH:  16
            (B) TYPE:  Amino Acid
            (C) STRANDEDNESS:  Unknown
            (D) TOPOLOGY:  linear (ii) MOLECULE TYPE: peptide (xi) SEQUENCE DESCRIPTION: SEQ ID NO: 3:

Ala Val Asp Thr Ala Glu Ala Gly Lys Lys Glu Lys Pro
 1               5                  10

Glu Lys Lys
     15
```

(2) INFORMATION FOR SEQ ID NO: 4:

(i) SEQUENCE CHARACTERISTICS:
        (A) LENGTH: 143
        (B) TYPE: Amino Acid
        (C) STRANDEDNESS: Unknown
        (D) TOPOLOGY: linear (ii) MOLECULE TYPE: peptide (xi) SEQUENCE DESCRIPTION: SEQ ID NO: 4:

```
Ala Val Asp Thr Ala Glu Ala Gly Lys Lys Glu Lys Pro
 1               5                  10
Glu Lys Lys Val Lys Lys Ser Asp Cys Gly Glu Trp Gln
    15                  20                  25
Trp Ser Val Cys Val Pro Thr Ser Gly Asp Cys Gly Leu
            30                  35
Gly Thr Arg Glu Gly Thr Arg Thr Gly Ala Glu Cys Lys
 40                  45                  50
Gln Thr Met Lys Thr Gln Arg Cys Lys Ile Pro Cys Asn
        55                  60                  65
Trp Lys Lys Gln Phe Gly Ala Glu Cys Lys Tyr Gln Phe
                70                  75
Gln Ala Trp Gly Glu Cys Asp Leu Asn Thr Ala Leu Lys
 80                  85                  90
Thr Arg Thr Gly Ser Leu Lys Arg Ala Leu His Asn Ala
            95                 100
Glu Cys Gln Lys Thr Val Thr Ile Ser Lys Pro Cys Gly
105                 110                 115
Lys Leu Thr Lys Pro Lys Pro Gln Ala Glu Ser Lys Lys
        120                 125                 130
Lys Lys Lys Glu Gly Lys Lys Gln Glu Lys Met Leu Asp
                135                 140
```

(2) INFORMATION FOR SEQ ID NO: 5:

(i) SEQUENCE CHARACTERISTICS:
        (A) LENGTH: 995
        (B) TYPE: Nucleotide
        (C) STRANDEDNESS: Unknown
        (D) TOPOLOGY: linear (ii) MOLECULE TYPE: cDNA for cRNA (xi) SEQUENCE DESCRIPTION: SEQ ID NO: 5:

```
GGGAGGGAGA GCGCCCAGCC TTCGTCCTCC TGGCCCGCTC          40
CTCTCATCCC TCCCATTCTC CATTTCCCTT CCGTTCCCTC          80
CCTGTCAGGG CGTAATTGAG TCAAAGGCAG GATCAGGTTC         120
CCCGCCTTCC AGTCCAAAAA TCCCGCCAAG AGAGCCCCAG         160
AGCAGAGGAA AATCCAAAGT GGAGAGAGGG GAAGAAAGAG         200
ACCAGTGAGT CATCCGTCCA GAAGGCGGGG AGAGCAGCAG         240
CGGCCCAAGC AGGAGCTGCA GCGAGCCGGG TACCTGGACT         280
CAGCGGTAGC AACCTCGCCC CTTGCAACAA AGGCAGACTG         320
AGCGCCAGAG AGGACGTTTC CAACTCAAAA ATGCAGGCTC         360
AACAGTACCA GCAGCAGCGT CGAAAATTTG CAGCTGCCTT         400
```

-continued

| | |
|---|---|
| CTTGGCATTC ATTTTCATAC TGGCAGCTGT GGATACTGCT | 440 |
| GAAGCAGGGA AGAAAGAGAA ACCAGAAAAA AAAGTGAAGA | 480 |
| AGTCTGACTG TGGAGAATGG CAGTGGAGTG TGTGTGTGCC | 520 |
| CACCAGTGGA GACTGTGGGC TGGGCACACG GGAGGGCACT | 560 |
| CGGACTGGAG CTGAGTGCAA GCAAACCATG AAGACCCAGA | 600 |
| GATGTAAGAT CCCCTGCAAC TGGAAGAAGC AATTTGGCGC | 640 |
| GGAGTGCAAA TACCAGTTCC AGGCCTGGGG AGAATGTGAC | 680 |
| CTGAACACAG CCCTGAAGAC CAGAACTGGA AGTCTGAAGC | 720 |
| GAGCCCTGCA CAATGCCGAA TGCCAGAAGA CTGTCACCAT | 760 |
| CTCCAAGCCC TGTGGCAAAC TGACCAAGCC CAAACCTCAA | 800 |
| GCAGAATCTA AGAAGAAGAA AAAGGAAGGC AAGAAACAGG | 840 |
| AGAAGATGCT GGATTAAAAG ATGTCACCTG TGGAACATAA | 880 |
| AAAGGACATC AGCAAACAGG ATCAGTTAAC TATTGCATTT | 920 |
| ATATGTACCG TAGGCTTTGT ATTCAAAAAT TATCTATAGC | 960 |
| TAAGTACACA ATAAGCAAAA ACAACCAATT TGGGT | 995 |

(2) INFORMATION FOR SEQ ID NO: 6:

(i) SEQUENCE CHARACTERISTICS:
        (A) LENGTH: 21
        (B) TYPE: Nucleotide
        (C) STRANDEDNESS: Unknown
        (D) TOPOLOGY: linear (ii) MOLECULE TYPE: DNA (genomic)

(xi) SEQUENCE DESCRIPTION: SEQ ID NO: 6:

| | |
|---|---|
| GCTGAAGCAG GGAAGAAAGA G | 21 |

(2) INFORMATION FOR SEQ ID NO: 7:

(i) SEQUENCE CHARACTERISTICS:
        (A) LENGTH: 29
        (B) TYPE: Nucleotide
        (C) STRANDEDNESS: Unknown
        (D) TOPOLOGY: linear (ii) MOLECULE TYPE: DNA (genomic)

(xi) SEQUENCE DESCRIPTION: SEQ ID NO: 7:

| | |
|---|---|
| GGTCTCGAGT ATGTTCCACA GGTGACATC | 29 |

(2) INFORMATION FOR SEQ ID NO: 8:

(i) SEQUENCE CHARACTERISTICS:
        (A) LENGTH: 21
        (B) TYPE: Nucleotide
        (C) STRANDEDNESS: Unknown
        (D) TOPOLOGY: linear (ii) MOLECULE TYPE: DNA (genomic)

(xi) SEQUENCE DESCRIPTION: SEQ ID NO: 8:

| | |
|---|---|
| GGGAAGAAAG AGAAACCAGA A | 21 |